(12) United States Patent
Pratt

(10) Patent No.: US 6,236,743 B1
(45) Date of Patent: May 22, 2001

(54) THREE-DIMENSIONAL DIGITIZING SYSTEM AND METHOD

(76) Inventor: Greg Pratt, 12642 SW. 94th Pl., Miami, FL (US) 33176

(*) Notice: Subject to any disclaimer, the term of this patent is extended or adjusted under 35 U.S.C. 154(b) by 0 days.

(21) Appl. No.: 09/116,073

(22) Filed: Jul. 15, 1998

Related U.S. Application Data

(63) Continuation-in-part of application No. 09/037,295, filed on Mar. 9, 1998, which is a continuation-in-part of application No. 08/528,979, filed on Sep. 15, 1995, now Pat. No. 5,781,652.
(60) Provisional application No. 60/039,943, filed on Mar. 10, 1997.

(51) Int. Cl.[7] .................................................. G06K 9/00
(52) U.S. Cl. ............................. 382/128; 33/512; 382/154
(58) Field of Search ................................... 382/100, 103, 382/108, 128, 141, 145, 146–154; 345/430; 356/496, 500, 489; 600/587; 606/1; 700/193; 33/512

(56) References Cited

U.S. PATENT DOCUMENTS

| | | | |
|---|---|---|---|
| 5,287,273 | * | 2/1994 | Kupfer et al. .................... 128/653.4 |
| 5,351,196 | * | 9/1994 | Sowar et al. ..................... 364/474.24 |
| 5,951,475 | * | 9/1999 | Gueziec et al. ....................... 600/425 |
| 6,047,080 | * | 4/2000 | Chen et al. ........................... 382/128 |

* cited by examiner

*Primary Examiner*—Jay Patel
(74) *Attorney, Agent, or Firm*—Malloy & Malloy, P.A.

(57) ABSTRACT

A three-dimensional digitizing system and method preferably to be useable for the manufacture of a precisely configured clinical support device such as an orthotic brace and/or a prosthetic limb. The digitizing system includes at least one probe which is to be passed over a portion of a three-dimensional body to be digitized, the probe including an exterior housing of known dimensions and being structured to have a position element disposed therein. The position element is structured to provide specific six-degree of freedom position and orientation information relative to a reference element which is also included in the digitizing system. As such, the specific position and orientation of the probe relative to the reference element is determined and any volume relative to the reference element through which any portion of the probe is passed is determined and stored by the digitizing system so as to determine an exact shape of the three-dimensional body from the identification of all volumes through which the probe has not passed due to the physical presence of the body being mapped.

16 Claims, 1 Drawing Sheet

THREE-DIMENSIONAL DIGITIZING SYSTEM AND METHOD

The present is a continuation-in-part of co-pending U.S. patent application Ser. No. 09/037,295, filed on Mar. 9, 1998 which claims priority under U.S.C. Section 119(e) to U.S. Provisional patent application filed on Mar. 10, 1997 and assigned Ser. No. 60/039,943; which is a continuation-in-part application of application of U.S. patent application Ser. No. 08/528,979 filed Sep. 15, 1995, issued as U.S. Pat. No. 5,781,652 on Jul. 14, 1998.

BACKGROUND OF THE INVENTION

1. Field of the Invention

The present invention relates to a three dimensional digitizing system, to be used primarily for the determination of the precise shape of a three dimensional body, such as a patient's body part that is in need of an effective, precision fitted, support socket for a clinical support device such as an orthotic brace and/or a prosthetic limb, and can be used conveniently and effectively with bodies that cannot be fitted, readily moved or re-positioned into a cast/mold or specialized laser/photographic scanner type device.

Further, the present invention relates to a method of precisely defining the shape and contour of a portion of a three dimensional body, such as for the formation of a support socket of a clinical support device in a manner which provides for minimal trial and error, and is comfortable and convenient to implement in a variety of situations and orientations.

2. Description of the Related Art

In a variety of specialized industries, there is a need to identify and define the precise shape and configuration of all or a portion of a three dimensional body. That three dimensional body may include an artifact, structure or part to be duplicated or mated with, a human body part to be reproduced or supported, or any other physical object to be identified with precision. Presently, the most common way of determining and utilizing the desired shape and contour requires the making of a mold of the body in question. For example, plastic or wax molds or impressions are frequently used with inanimate or easily manipulable objects. Resent technology has, however, permitted the use of laser scanning or other mechanical devices to receive the body to be scanned, and thereby use laser refraction and reflectivity to map out the precise shape and contour of the three dimensional body. While such molding or laser scanning techniques have proven generally effective with many three dimensional bodies and in many applications, there are still a number of attendant drawbacks associated with their use.

Specifically, one primary disadvantage associated with known scanning systems involves the scanning environment. In particular, conventional laser or ultrasound digitizing systems require the body to be analyzed to be located within a precision environment that is part of the device itself. Moreover, the orientation and position of the body must be constantly maintained for an extended period of time. While these procedures may be acceptable with smaller bodies, when larger or animate bodies are the subject of digitizing, it can become very difficult and costly to bring the body to the digitizer and fit the body into the necessary pre-defined parameters of the digitizer.

An alternative to the confined operating environments of such laser or ultra sound digitizers involves point by point digitizing. These systems typically employ a pointer or other device to plot certain predefined and necessary points on a body to be digitized. From these points, the remaining structure can be extrapolated by a computer system and a rough image is generated. Unfortunately, however, such systems are very time consuming to utilize, requiring many individual points to be independently plotted if an accurate image is to be generated, and even if a number of points are plotted, minor variations between the plotted points are generally not accounted for in an accurate manner. Furthermore, such systems require complete stability of the position and orientation of the body being digitized in order to maintain proper reference.

Accordingly, there is a need for a digitizing system that is portable, does not require an elaborate and predefined environment in order to precisely digitize any shape or sized body in an accurate manner. Further, such a device should actually take into account the contours of the body, not relying on computerized extrapolation to define an approximation of the shape of the body.

By way of example, an important and prevalent application of the need for precision identification of the shape and configuration of a three dimensional body relates to the prosthetic and orthotic fields of medicine wherein precise, customized clinical support devices, such as prosthetic limbs or orthotic braces, must often be constructed to correspond to unique and very specific shapes. In these applications, as in the various other related and unrelated applications, the desire to determine the precise shape of all or part of a three-dimensional body, such as the human body part to be supported, is quite necessary and often quite critical to the formation of an effective mold, model, or mating part, such as the support socket of the clinical support device. For example, in the case of a prosthetic limb, the support socket is generally adapted to be fitted over the terminal portion of a patient's limb in order to act as a replacement for the missing limb. As such, a precise fit is necessary because a substantial amount of constant pressure is going to be exerted on the terminal end of the limb as the clinical support device is utilized. Specifically, most portions of the human body are not capable of withstanding constant focused pressure thereon for extended periods of time. This factor therefore necessitates that in the definition and formation of the support socket of the clinical support device, the pressure that will be exerted from the support device to the patient be spread out as much as possible, thereby preventing any concentrated or focused pressure on any one portion of the terminal end of the limb.

Currently in the prosthetic/orthotic field of art, it is substantially difficult to use known devices and methods to define the necessary configuration without substantial time and effort being put into initial molding and various revised moldings of the support socket of the clinical support device.

This factor alone has made the conventional art relating to the formation of clinical support devices very specialized, with the practitioners often being highly skilled craftsmen with extensive years of training and experience. Specifically, because prior art systems and methods of defining the support socket are so imprecise, the extensive training and experience is necessary in order for the practitioner to get a feel for their patients' needs merely by viewing the patient and analyzing a conventional plaster type mold or photographically scanned image, and to recognize what the results of minor changes or modifications to the mold will be after viewing the pressure points which result after trial of an initial molded support socket. As is evident, such trial and error molding is not only time consuming and inconvenient for the patient, but can also become quite expensive due to the labor intensive nature of the work and the need to have a highly skilled practitioner. Accordingly, there is a need in the art to provide a system and method that can substantially facilitate the formation of a clinical support device while also increasing the precision of the form of an initially constructed support socket.

Continuing further with the example of the field of art relating to the formation of clinical support devices, there are presently three existing methods of shape capture that are utilized to define the support socket of a clinical support device. The first, most commonly used method simply involves the formation/molding of a plaster cast to capture the shape of the applicable body part. Once the plaster cast is taken, it is removed from the patient and filled with plaster to form a positive mold. The practitioner will then call upon their experience and/or best guess to guide them in adding or removing plaster by hand in order to modify the shape taken during casting and thereby create a final shape. As such, the final shape is truly a combination of the molded shape and the practitioner's skill and experience in determining where certain modifications should be made. A final plaster shape is then made and draped in some manner with heated plaster or laminate to create the finished support device. Unfortunately, however, in addition to being imprecise, and ineffective to provide any concrete information regarding pressure distribution, this conventional method can often be quite difficult or uncomfortable to implement. Specifically, because clinical support devices are often formed for use after a patient leaves the hospital and has undergone various procedures, it is often difficult to move a patient to a location where the molds can be made. Also, while the patient is in the hospital they may have various tubes or other devices connected with their body that make the formation of cast mold substantially difficult, if not completely impossible. Further, such conventional casting does not provide for any information regarding the three-dimensional shape of the limb in various flexed positions, a criteria that can be quite important to maintain the overall comfort and effectiveness of the clinical support device formed as the pressure points may change during flexing.

A second commonly utilized approach in the formation/definition of a support socket of a clinical support device includes the implementation of computer assisted formation with casting. Generally, in this method a plaster cast is taken of the patient in the same manner as the conventional casting method. The computerized imaging system is then used to take an image of the plaster cast either by mechanical or optical means. In particular, the cast is utilized to obtain the image because most conventional imaging systems require specific positioning of an object/body to be scanned, and often require extensive manipulation and re-orientation of the object being scanned. Once scanned by the computer, the practitioner can avoid the step of manually modifying the shape by making the estimated modifications utilizing the computer. From there, the final shape can be cut by a milling machine so as to form the physical model into a foam or plaster blank. This final foam or plaster shape is then draped in some manner with heated plaster or laminate to create the finished clinical support device to be used on the patient. As is evident from the description of this method, casting, a procedure which, as previously mentioned, can be inconvenient or difficult to accurately utilize, is still necessary to provide the initial frame work to be manipulated and captured as a computerized image. Further, the practitioner must still utilize trial and error along with their skill and experience to reconfigure the formed socket.

A final method associated with the creation of a clinical support device includes what is known as direct imaging. Direct imaging generally includes an optical sensor, which naturally takes a number of optical/picture images of the body parts to be supported, and often uses specialized laser guiding methods to define the precise area to be captured. Alternatively, some medical facilities utilize CT scans, MRI's or ultrasonic methods to accomplish the same results. These direct imaging devices, as well as those implemented in various other applications generally require a special facility or layout, and if some flexibility is available to probe the patient, the final image is often a result of a series of extrapolations taken from numerous reference points obtained through a light pen or other pointer. Further, regardless of the direct imaging system employed, once the computerized image is captured, the scanned image is merely utilized as a computer model to which the practitioner can make the estimated or "best guess" modifications for the formation of the foam plaster blank used in the fabrication of the finished appliance.

Therefore, it is evident that the various systems/methods which are currently employed in the art have a number of serious drawbacks associated therewith. A first, and very significant drawback which is sought to be overcome with the system and method of the present invention relates to the inability of prior methods and devices to assist with the equalization of pressure throughout the finished support device, or at least to create smooth pressure variations from one area to the next. In fact, because as previously recited, a person's body parts are generally not capable of withstanding constant pressure, equalization of the pressure points throughout the finished support device, or at least the creation of smooth pressure variations from one area of the support socket to the next is one of the primary objectives in the field of prosthetics and orthotics, and has therefore turned many practitioners to exploring any method available to get some indication to assist with the determination of the necessary modifications. For example, practitioners utilizing the conventional methods attempt to "pre-load" the patient's musculature as much as possible in order to help distribute pressures equally in the final socket or appliance. This procedure, however, is substantially time consuming and in the end educated guesses, which are subject to human error, are still necessary. Accordingly, it is inevitable that when conventional pre-loading techniques are implemented, it is only later, during the modification and fitting stages, and after substantial trial and error, that the final equalization of surface pressures is accomplished. Further, such conventional methods much often rely on physical indicators such as reddening or blanching of the skin which is being supported to provide some indication of adjustments that should be made to appropriately equalize the pressure. Such physical indicators are not only imprecise, but can be painful to the patient. Still, however, because these pre-loading methods are better than nothing, the prior art methods which utilize casting are generally preferred over known direct imaging methodologies wherein no method for pre-loading the patient's musculature is available.

An additional drawback associated with all prior art methods of forming a support device is the fact that only one "snapshot" is taken from the patient. Because only one "snapshot", either through casting or direct imaging is available, the practitioner's ability to determine how the patient's flesh will deform and resist pressure during the modification phases or during a flexing of the patient's body is substantially limited.

Still another drawback associated with conventional devices relates to site and circumstance restrictions. Specifically, utilizing conventional devices/methods the practitioner is generally restricted to a particular location or facility wherein the plaster cast can be appropriately taken and maintained, or to a particular location where the large, often highly expensive direct imaging device is located. Further, it is a common occurrence regarding postoperative patients that casting will be unavailable, especially when a body-jacket is necessary, because of the intravenous tubes, drains, and other equipment that must be left undisturbed and connected with the patient. Such circumstances similarly prevent the direct imaging methods, as the various equipment connected with the patient can significantly interfere with the taking of an accurate image. Also, with regard to direct imaging, the most common of which are optics based, certain shadowing is often experienced as the scanner cannot appropriately obtain an image of hidden areas, such as the patient's ischium or ramus which are critical to a correct fit for an above the knee support device.

Yet another drawback associated with conventional methods of forming a clinical support devices relates to the axial limitations. Generally, with most conventional methods, there is an implied single axis center line which must be given consideration when forming the support device. Unfortunately, however, in some circumstances such as during the formation of an ankle-foot orthosis, it may be impossible for the patient to have a single centerline running through the body portion to be captured. Similarly, the computer assisted capture methods are generally ineffective when a single center line cannot be drawn through the cast or through the entire body portion to be scanned.

Accordingly, there is a substantial need in the art for an improved digitizing system which enables precise surface images of a three-dimensional body, such as a body part of an individual, to be conveniently and precisely determined in virtually any circumstance or patient location. Additionally, it would be highly beneficial to provide a digitizing system and method of manufacturing a support device which is able to provide for immediate modification, provide precise images, and enable the construction of a precise pressure distributing support device without substantial trial and error, or guess work on the part of the practitioner. The device of the present invention is designed precisely to meet these needs as well as the needs of other imaging applications wherein a quick, convenient, yet precise three dimensional image must be determined and/or when precise determination of the deformability of a three dimensional body under pressure is necessary.

SUMMARY OF THE INVENTION

A three-dimensional, support socket digitizing system, the digitizing system including at least one probe structured and disposed to be passed over, in contact with, a surface of a three-dimensional body such as a portion of the body to be supported or mated with by a corresponding socket. The probe itself includes an exterior housing of known dimension and contains a tracking assembly therein. Specifically, the tracking assembly, preferably a six-degree of freedom tracking assembly, includes a reference element and a position element, and is structured and disposed to calculate a six-degree of freedom position and orientation of the position element relative to the reference element. As such, the position element is disposed in the housing of the probe and is structured to provide reference data regarding a position and orientation of the probe at all times.

The digitizing system further includes a processing assembly which compares the reference data regarding the position and orientation of the probe with the known dimensions of the probe, thereby determining a volume, relative to the reference element, through which any portion of the probe is passed. Finally, an image mapping assembly stores all of the volumes relative to the reference element through which any portion of the probe is passed so as to determine an exact shape of the three-dimensional body as that volumes through which no portion of the probe had passed.

Further, the present invention relates to a method of forming mapping of at least a portion of a three-dimensional body in order to identify a precise shape and contour of that portion of the body, such as for the formation of a support socket of a clinical support device including an orthotic brace and/or a prosthetic limb. The method includes a first step of defining a reference volume which is arbitrarily greater than a volume of the support socket to be formed. Next, a probe of known volume and connected with a tracking device is passed over, in contact with, the corresponding portion of the body. Preferably, the probe is passed such that substantially every part of the portion of the body to be mapped is engaged by at least a portion of the probe. Every volume in space through which any portion of the probe passes is then identified.

Subsequently, all of those volumes through which any portion of the probe has passed are subtracted from the reference volume until the volume corresponding to the portion of the body being mapped remains. From this volume, a support surface to effectively support engage or model the volume is defined. Finally, in the case of an orthotic or prosthetic application, the support socket of the clinical support device is formed to correspond the defined support surface.

It is an object of the present invention to provide an improved digitizing system which does not merely rely upon a single point, or a probe tip, to provide a series of plotting points used to extrapolate a three-dimensional body, but rather will utilize the entire surface area of the probe to affirmatively determine every contour of the three-dimensional object.

A further object of the present invention is to provide an improved digitizing system which permits the accurate mapping of a three-dimensional body's surface contour even if the body moves during the mapping process.

Another object of the present invention is to provide an improved digitizing system which is substantially compact and portable, and is easy is to utilize in virtually any circumstance regardless of any tubes, wires, or other appliances connected with the three-dimensional object.

Still another object of the present invention is to provide an improved support socket digitizing system which is able to effectively and precisely determine and provide a localized or overall iso-pressure surface for the support socket in order to evenly and effectively distribute pressures along the portion of the body to be supported.

Also an object of the present invention is to provide an improved digitizing system which facilitates the determination of the depth of a deformation and the pressure required to make that deformation in a three-dimensional body.

Another object of the present invention is to provide an improved digitizing system which facilitates the formation of a clinical support device without substantial trial and error.

A further object of the present invention is to provide a method of forming a support socket of a clinical support device which is substantially simple and easy to perform by an orthotic or prosthetic technician, and which provides for the definition and formation of a substantially precise support socket of the clinical support device.

Also an object of the present invention is to provide an improved digitizing system which can capture information on the shape of a three-dimensional body from any available source including directly from a human patient, a patient's existing support device, a formed plaster model, or a plaster cast, either for independent use or for comparison with additional flexed or relaxed probing of the individual.

Another object of the present invention is to provide an improved digitizing system which permits a practitioner to deform a three-dimensional body at will during the shape capture process so as to permit the incorporation of shape modifications while the three-dimensional body is still available for precise placement.

A further object of the present invention is to provide an improved digitizing system which permits the capture of a three-dimensional body's surface contour, whether the object is solid or deformable, with a hand-held portable device.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
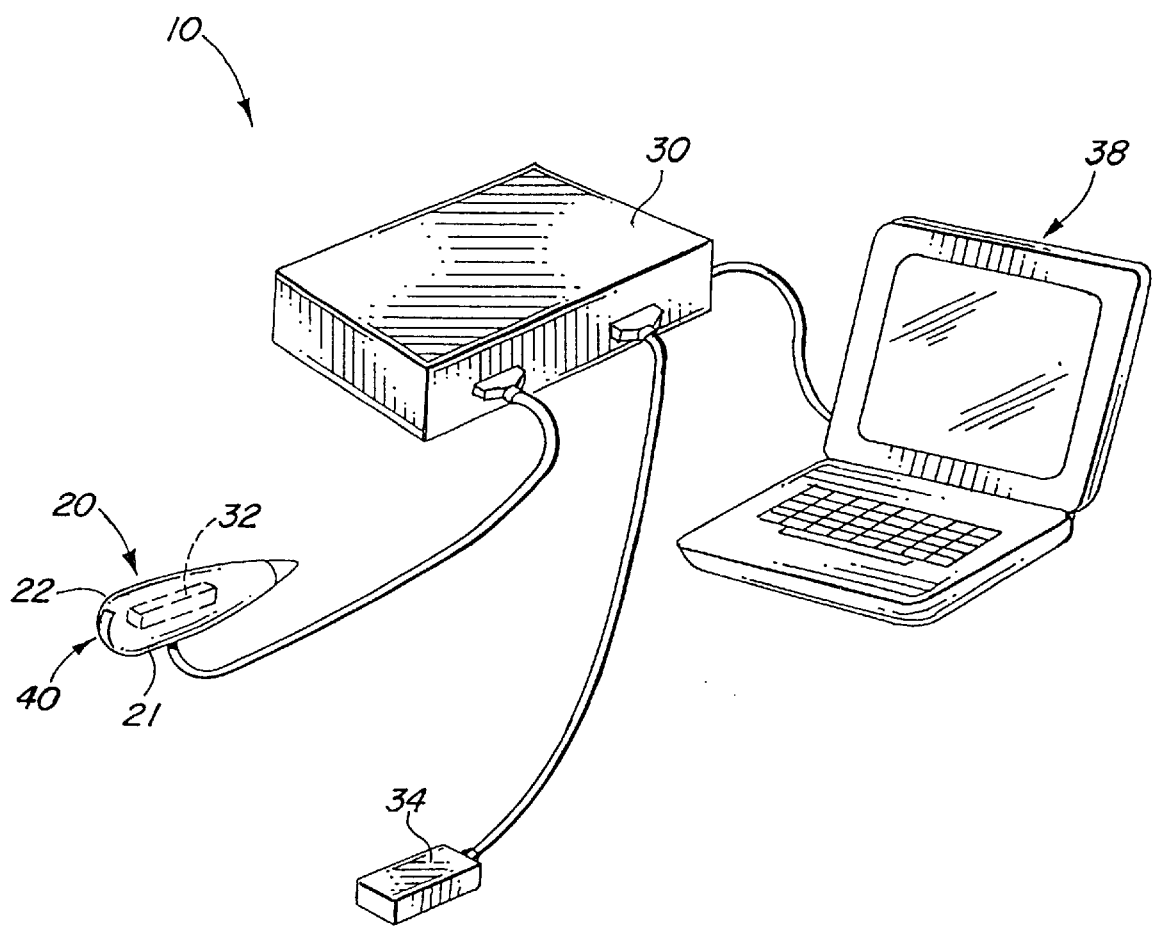
FIG. 1 is a perspective view of the digitizing system of the present invention.

As shown in the drawings, the present invention is directed towards an improved three-dimensional digitizing system, generally indicated as 10. In the preferred embodiment, the digitizing system 10 is a support socket digitizing system structured for use in the design and manufacture a precisely configured clinical support device, such as an orthotic brace and/or a prosthetic limb, and especially to configure the support area or support socket of the clinical support device which comes into contact with the patient. In particular, patients who have lost a limb, or patients with bone degenerative diseases or other physical afflictions, often require a prosthetic limb to replace their lost limb, or an orthotic brace to prove added support and stability. With the substantial advances that have been made in these various fields of art, the clinical support devices are becoming more and more advanced and helpful to the patient, and in fact often approach the capabilities of a normal limb. Unfortunately, however, an important and significant difficulty still remains. That difficulty relates to the definition and formation of a precisely fitting support socket of the clinical support device to be used on the patient. The main reasons for this difficulty relate to the need to have an exacting, secure fit, while avoiding any sensitive areas, and the pain and/or discomfort that can arise if the pressure exerted by the support device on the patient is focused at one or more specific points along the portion of the body being supported. Of course, it is noted that the present system can be utilized to digitize or map the precise shape and contour of any three dimensional body, whether animate or in-animate.

Turning specifically to the digitizing system 10 of the present invention, it includes at least one probe 20 which is structured and disposed to be passed over the three-dimensional body, such as a limb or portion of the body to be supported in the prosthetic and/or orthotic fields. This probe 20, which can take on any of a variety of configurations such as a wand type shape, a knob or fingertip type shape or the preferred rounded and pointed rectangular shape, includes an exterior housing 21 of precisely known dimensions. Further, the probe 20 is preferably made of substantially rigid, solid construction, and can include an open or hollow interior portion. Further, the preferred embodiment of the probe 20 includes at least one blunt-end portion and a pointed portion such that at least some portion of the probe 20 can be passed over every part/surface of the three-dimensional body whose image is being obtained.

Also included in the digitizing system of the present invention is a tracking assembly, such as a six-degree of freedom tracking assembly or device 30. The six-degree of freedom tracking assembly 30, which can take on any number of configurations, includes at least a reference element 34 and a position element 32. In use, the tracking assembly 30 determines a six-degree of freedom position and orientation of the position element 32 relative to the reference element 34. In particular, the six-degree of freedom tracking means 30 provide the precise position of the position element in the X, Y, and Z planes, as well as its orientation such as through its azimuth, elevation, and roll, thereby allowing the determination of the exact location and attitude of the position element 32 at all times. In the preferred embodiment, the six-degree of freedom tracking assembly 30 include an electromagnetic 3D-receiver such as those normally utilized in virtual reality applications. Still, however, alternative six-degree of freedom tracking assembly such as ultrasonic transducers, optical scanners and/or mechanical linkages can also be affectively employed so long as the precise position and orientation of the position element 32 is determined thereby.

The position element 32 of the tracking assembly 30 is structured to be disposed in operative association, preferably on or within the housing 21 of the probe 20. Accordingly, once the position element 32 is disposed in a known position and orientation with the probe 20, reference data regarding the position and orientation of the probe 20 can be determined.

The present invention further includes a processing assembly, such as a personal computer. The processing assembly is structured to compare the reference data regarding the position and orientation of the probe 20 with the known dimensions of the probe 20 so as to determine the specific volume in space, relative to the reference element 34, which is occupied at any given time by any portion of the probe 20. Accordingly, as the probe 20 is passed over the surface of a three dimensional body, or is merely moved through space, any volume through which any portion of the probe 20 passes is known and identified.

So as to effectively utilize the information obtained, the present invention also includes an image mapping assembly, also preferably the personal computer, which stores all of the volumes relative to the reference element 34 through which any portion of the probe 20 is passed in order provide for the determination of an exact shape of the three-dimensional body. Specifically, because the probe 20 cannot pass through a solid object, and specifically through the subject three-dimensional body, by passing the probe 20 over all of the relevant surfaces of the three-dimensional body, including every contour and crevasse, a precise, specific image relating to the three-dimensional body is provided from the volumes through which the probe 20 has not passed due to the physical presence of the three-dimensional body. Further, unlike conventional devices which must make modifications after the fact, the present invention allows for the accurate and effective formation of any desired modifications or variations to the normal shape utilizing the probe 20 to trace out the modification in space relative to the subject three dimensional object while the three-dimensional body is still in hand and can be used as a precise reference.

It is also noted that in the preferred embodiment of the present invention the volumes through which any portion of the probe 20 is passed is identified in relation to a three dimensional position and orientation of the portion of the three dimensional body being mapped. As such, changes in the orientation and position of the body being mapped while the probe 20 is being passed thereover and relative thereto will not affect the image being obtained. In order to maintain this optimal frame of reference, the present system further comprises a referencing assembly whereby the identified volumes through which any portion of the probe has passed are adjusted to reflect the changes in the position and orientation of the body and an accurate image is obtained. In the preferred embodiment, the referencing assembly includes the securement of the reference element 34 in a fixed position to the body being mapped. In particular, because the position and orientation information provided by the positioning element are preferably generated relative to the reference element. A continuous positioning of the reference element 34 relative to the body being mapped will compensate for movement of the body such that the volume through which any portion of the probe 20 is passed remains consistent relative to the body. In a preferred embodiment a secure strap mechanism that prevents sliding or movement relative to the body is preferred, and in the described orthotic/prosthetic embodiment the strap can be secured around the limb being mapped, such as the thigh area.

Additionally, the preferred embodiment of the present invention also includes a shaping assembly. Specifically, once the exact shape of the three-dimensional body, and any affirmatively defined modifications, are provided by the image mapping assembly, the shaping assembly of the present invention can form a precise, three-dimensional shape which corresponds it precisely. Generally, the resultant, precise three-dimensional shape is the shape of the support socket of the clinical support device which is to be fabricated.

Further, the present invention also preferably includes or can be connected to a computer controlled milling machine. In particular, information regarding the precise three-dimensional shape defined/formed by the shaping assembly is transmitted via a standard input/output connection to the computer control of a milling machine. The milling machine can then, in a conventional manner, specifically and precisely cut the desired three-dimensional shape to produce the shape of the desired support socket.

Accordingly, utilizing the probe 20 of the present invention all portions of the body must merely be rubbed by any portion of the probe 20, and any tubes, wires or other appliances connected with a patient can be worked around by the probe 20 with a space filled in subsequently.

Additionally, included in the preferred embodiment of the digitizing system of the present invention is a pressure sensing assembly generally indicated as 40. While the pressure sensing assembly 40 may take on any of the number of structures and configurations, in the preferred embodiment the pressure sensing assembly 40 includes a calibrated force sensing resistor. Specifically, the calibrated force sensing resistor, which is generally small and lightweight, is disposed in a surface of the housing of the probe 20, and preferably at a blunt tip of the probe 20. In use, the pressure sensing assembly 40, and in particular the force sensing resistor, is structured and disposed to determine a pressure exerted by the blunt end of the probe on the three-dimensional body. Accordingly, in use, the probe 20, and preferably its blunt end wherein the pressure sensing assembly 40 is disposed, is utilized to deform the three-dimensional body. Utilizing the image mapping assembly, the position of any area of the probe 20 within a preferably predefined exterior surface of the three dimensional object is known, and as such the precise depth and shape of the deformation which is formed by the probe 20 is precisely known. Additionally, because the portion of the probe 20 including the pressure sensing assembly 40 is utilized, the pressure exerted by the probe 20 on the three-dimensional body so as to achieve the known deformation is also determined. Such information is invaluable in the configuration and formation of the support socket of a clinical support device as it allows a practitioner to work within known parameters in order to achieve their objective, unlike conventional methods which rely greatly on practitioner experience and trial and error to achieve the same results.

In order to utilize the pressure and deformation information gathered effectively, the information is preferably transmitted to a pressure mapping assembly, also preferably included in the digitizing system of the present invention. The pressure mapping assembly is structured to compare the pressure exerted by the probe on the three-dimensional body with the deformation formed. In many conventional applications, such as product testing, the strength of a specific deformable material can be determined, as well as the pressure resistance at various portions of a three-dimensional body. Further, in such fields as the physical fitness area, muscle tone can be determined by periodic testing and the determination of the muscles' increased resistance to deformation under certain loads. Still, however, the most beneficial use relates to the field of prosthetic and/or orthotic medicine wherein the clinical support device is manufactured. In this application, the pressure mapping assembly is able to utilize the information regarding the amount of deformation and pressure exerted to cause that deformation, either alone or with similar information regarding the same point in different flexed and unflexed orientations, so as to define a perfect iso-pressure surface based on the previously mentioned known parameters. The perfect iso-pressure surface, when formed into the precise three-dimensional shape from which the support socket is defined, is structured to evenly distribute pressure over an entire area of the three-dimensional object. Further, the pressure can be calculated not only in a static mode, but also when the clinical support device is being utilized throughout a full range of movement of a patient. Accordingly, the step of crude pre-loading and guess work with regard to the effects of different contours and configurations is eliminated as the precise pressure/deformation result is known before the fact and the support socket which is formed initially takes all such information into account.

As indicated, the processing assembly, image mapping assembly, and pressure mapping assembly can all be included in small, portable laptop type computer 38 which can be easily transported in conjunction with the six-degree of freedom tracking assembly. With regard to the specific calculations and comparisons to be made, it is noted that all are mathematical functions and can be implemented utilizing a variety of programs and calculations which interpret the information that is collected for processing by the improved digitizing system of the present invention. Further, it should also be noted that while the preferred embodiment of the digitizing system of the present invention utilizes iterative volume subtraction to subtract all the volumes through which any portion of the probe 20 passes from an initial reference volume, the reference shape may also be an open space which is formed by the addition of a solid at all areas through which the probe is passed. Within the context of this invention, this is referred to as iterative volume addition. Additionally, in the preferred embodiment of the present invention, the digitizing system is structured to perform both iterative volume subtraction and iterative volume addition which can be substantially helpful in the modification stages wherein specific, affirmatively defined modifications are to be formed in addition to the exact shape of the three-dimensional body.

The present invention is also directed towards a method of mapping at least a portion of a three-dimensional body in order to identify a precise shape and contour of that portion of the body, such as in a preferred application for the formation of a support socket of a clinical support device, such as an orthotic brace and/or a prosthetic limb, utilizing the three-dimensional digitizing system of the present invention. The first step of mapping method is the definition of a reference volume which is greater than a volume of the body to be mapped. Next, a probe of known volume and containing a six-degree of freedom tracking device therein is passed over the portion of the body to be mapped. Preferably, the probe is passed in any random manner desired over the body part such that substantially every area of that portion of the body to be mapped is engaged by at least a portion of the probe. Concurrently, every area through which any portion of the probe is being passed is determined, and that area is subtracted from the reference volume until substantially only the precise shape and contour of the portion of the body to be mapped remains in the reference volume. Additionally, as previously noted the shape capture may include volume addition from an open space reference volume, which can also be viewed as iterative volume addition for clarity. In the orthotic and prosthetic application, the remaining volume defines a desired support area corresponding the portion of the patient's body to be supported.

In the preferred application, once the desired support area is determined, a support surface to effectively support that desired support area is defined. Preferably, an additional step of manipulating the probe to define at least one surface modification in the desired support area is also included so as to provide for substantially increased comfort and convenience to the wearer. For example, in certain circumstances portions of the body to be supported include various sensitive areas which are preferably maintained isolated from any engagement with the support socket. In these circumstances modifications can be made by manipulating the probe over the sensitive area in order to define the modification area. Further, because certain portions of the body, such as the ischial containment socket, require a substantially intimate fit with the clinical support device, utilizing the probe and method of the present invention the probe can be passed precisely over the contours of the body part while it is in both a flexed and unflexed orientation. This multiple probing functions to ensure proper support and/or clearance is maintained during a full range of movement of the patient. Further, even if the location of a desired modification is known by a practitioner using conventional casting and imaging methods, some substantial approximation and reworking is generally still required to properly and effectively position and size the modification.

Additionally, the method of the present invention preferably includes the additional step of deforming the portion of the body to be supported in at least one but preferably a plurality of points thereof. The deformation is performed directly with the probe, which preferably includes pressure sensing means therein. Accordingly, a pressure exerted by the probe on the body is determined and compared with an amount of deformation formed by the probe as determined as a result of the tracking means in the probe. By comparing the amount of deformation formed with the pressure exerted, and with the desired support area, a preferred iso-pressure surface is precisely defined. As previously recited, the perfect iso-pressure surface is structured to evenly distribute pressure over an entire area of the portion of the body with which the iso-pressure surface comes into supporting contact. Also, in the case of flexing or moving joints and/or muscles, the step can be performed a number of times with the same portion of the body to be supported in various states of flex or tension. This ensures that the iso-pressure surface functions appropriately during the full range of movement of the patient and provides a significant advantage over what can be accomplished utilizing known casting or imaging methods that must rely primarily on a practitioner's educated guesses and trial and error, a common source of delay, added expense and patient discomfort.

Finally, when the finished support surface to effectively support the desired support area has been defined, the support socket of the clinical support device is formed to correspond to it exactly.

While this invention has been shown and described in what is considered to be a practical and preferred embodiment, it is recognized that departures may be made within the spirit and scope of this invention which should, therefore, not be limited except as set forth in the claims which follow and within the doctrine of equivalents. Furthermore, it is noted that within the context of this invention it has been noted that the probe may be passed randomly over the three-dimensional body. This terminology has been utilize to indicate that no predefined path or point by point mapping is required, although if desired a practitioner or programmer could elect to follow a uniform path for reasons of ensuring that all areas have been covered and the like. As a result, the term random is seen to encompass such defined paths of movement.

Now that the invention has been described,
What is claimed is:
1. A three dimensional digitizing system comprising:
   at least one probe structured and disposed to be randomly passable over a portion of a body to be mapped,
   said probe including an exterior housing of known dimensions,
   a tracking assembly, said tracking assembly including a reference element and a position element, and being structured and disposed to substantially continuously calculate a position and orientation of said position element relative to said reference element,
   said position element of said tracking assembly being disposed in operative association with said housing of said probe and in a fixed position relative thereto so as to provide substantially continuous reference data regarding a position and orientation of said probe,
   a processing assembly structured and disposed to compare said reference data regarding said position and orientation of said probe with said known dimensions of said probe so as to determine a volume relative to said reference element through which any portion of said probe is passed, and an image mapping assembly structured and disposed to store all of said volumes relative to said reference element through which any portion of said probe is passed, and to define a substantially exact shape and contour of the portion of the body to be mapped by identifying all volumes through which no portion of said probe has passed due to a physical presence of said portion of said body to be mapped.

2. A three dimensional digitizing system as recited in claim 1 wherein said image mapping assembly subtracts all of said volumes relative to said reference element through which any portion of said probe is passed from a pre-defined reference volume such that only said exact shape and contour of the portion of the body and any affirmatively defined modifications remain.

3. A three dimensional digitizing system as recited in claim 1 wherein said tracking assembly, said processing assembly, and said image mapping assembly are substantially portable and compact.

4. A three dimensional digitizing system as recited in claim 1 wherein said probe is further structured to define any desired shape modifications in said shape of said portion of said body so as to facilitate the construction of a precisely shaped socket to be placed over said portion of said body.

5. A three dimensional digitizing system as recited in claim 1 wherein said housing of said probe includes a rigid shape of known dimensions.

6. A three dimensional digitizing system as recited in claim 1 further including a pressure sensing assembly disposed in said housing of said probe, said pressure sensing assembly being structured and disposed to determine a pressure exerted by said probe on the portion of the body.

7. A three dimensional digitizing system as recited in claim 6 wherein said image mapping assembly is structured to precisely determine a deformation formed in said portion of the body by said probe upon said probe exerting said pressure thereon.

8. A three dimensional digitizing system as recited in claim 1 further including a shaping assembly structured to be connected with said image mapping assembly, and structured to form a support socket which engages the portion of the body.

9. A three dimensional digitizing system as recited in claim 1 further comprising a referencing assembly structured to maintain said portion of the body to be mapped at a precise three dimensional position and orientation while said probe is being passed thereover.

10. A three dimensional digitizing system as recited in claim 1 wherein said volume through which any portion of said probe is passed is identified in relation to a three dimensional position and orientation of said portion of the body being mapped, and said system further comprises a referencing assembly structured to identify changes in said orientation and position of said portion of the body being mapped while said probe is being passed thereover and relative thereto, and to accordingly adjust said volume through which any portion of the probe has passed to reflect said changes.

11. A method of mapping at least a portion of a body in order to identify a precise shape and contour of said portion of the body being mapped, said method comprising the steps of:
defining a reference volume greater than a volume of the portion of the body being mapped,
randomly passing a probe of known volume and including a tracking device over said portion of the body to be mapped such that substantially all of the portion of the body to be mapped is at least temporarily engaged by at least a portion of said probe,
identifying every volume through which any portion of said probe is passed, and subtracting said volume through which any portion of said probe is passed from said reference volume until substantially only said precise shape and contour of the portion of the body to be mapped remains in said reference volume.

12. A method of mapping a portion of a body as recited in claim 11 further including the step of manipulating said probe to define at least one surface modification in said portion of the body to be mapped.

13. A method of mapping a portion of a body as recited in claim 12 further including the steps of:
deforming said portion of said body to be mapped at at least one point thereof with said probe, and
determining an amount of deformation in said portion of said body to be mapped that is formed by said probe, and a pressure exerted by said probe to result in said amount of deformation.

14. A method of mapping a portion of a body as recited in claim 13 wherein said step of deforming said portion of said body to be mapped at said at least one point thereof with said probe, further includes moving said portion of the body to be mapped into a plurality of flexed orientations and deforming said portion of said body to be mapped in each of said flexed orientations.

15. A three dimensional digitizing system comprising:
at least one probe structured and disposed to be passed over a portion of a body to be mapped,
said probe including an exterior housing of known dimensions,
a tracking assembly, said tracking assembly including a reference element and a position element, and being structured and disposed to calculate a position and orientation of said position element relative to said reference element,
said position element of said tracking assembly being disposed in operative association with said housing of said probe in a defined position so as to provide substantially continuous reference data regarding a position and orientation of said probe,
a processing assembly structured and disposed to compare said reference data regarding said position and orientation of said probe with said known dimensions of said probe so as to determine a volume relative to said reference element through which any portion of said probe is passed,
an image mapping assembly structured and disposed to store all of said volumes relative to said reference element through which any portion of said probe is passed, and to define an exact shape and contour of the portion of the body to be mapped by subtracting all of said volumes relative to said reference element through which any portion of said probe is passed from a pre-defined reference volume such that substantially only said exact shape and contour of the portion of the body to be mapped and any affirmatively defined modifications remain, and
a pressure sensing assembly disposed in said housing of said probe, said pressure sensing assembly being structured and disposed to determine a pressure exerted by said probe on the portion of the body to be supported.

16. A three dimensional digitizing system as recited in claim 15 wherein said reference element is secured to the body to be mapped such that said volume through which any portion of said probe is passed remains consistent relative to the portion of the body to be mapped upon changes in a position and orientation of the body to be mapped.

* * * * *